United States Patent
Jin et al.

(10) Patent No.: US 12,228,570 B2
(45) Date of Patent: Feb. 18, 2025

(54) ANALYTE QUANTITATION

(71) Applicant: UNIVERSITY OF TECHNOLOGY SYDNEY, Ultimo (AU)

(72) Inventors: Dayong Jin, Ultimo (AU); Hao He, Ultimo (AU)

(73) Assignee: UNIVERSITY OF TECHNOLOGY SYDNEY, Ultimo (AU)

( * ) Notice: Subject to any disclaimer, the term of this patent is extended or adjusted under 35 U.S.C. 154(b) by 911 days.

(21) Appl. No.: 17/279,576

(22) PCT Filed: Sep. 25, 2019

(86) PCT No.: PCT/AU2019/051034
§ 371 (c)(1),
(2) Date: Mar. 24, 2021

(87) PCT Pub. No.: WO2020/061632
PCT Pub. Date: Apr. 2, 2020

(65) Prior Publication Data
US 2021/0396746 A1    Dec. 23, 2021

(30) Foreign Application Priority Data
Sep. 25, 2018   (AU) ................................ 2018903614

(51) Int. Cl.
*G01N 33/543* (2006.01)
*G01N 33/53* (2006.01)

(52) U.S. Cl.
CPC ... *G01N 33/54388* (2021.08); *G01N 33/5302* (2013.01); *G01N 33/54346* (2013.01); *G01N 2333/705* (2013.01); *G01N 2458/40* (2013.01)

(58) Field of Classification Search
CPC ......... G01N 33/54388; G01N 33/5302; G01N 33/54346; G01N 2333/705; G01N 2458/40
See application file for complete search history.

(56) References Cited

U.S. PATENT DOCUMENTS

2006/0223197 A1   10/2006  Vielsack

FOREIGN PATENT DOCUMENTS

| CN | 105842464 A | 8/2016 |
| CN | 107525937 A | 12/2017 |
| CN | 108196044 A | 6/2018 |
| JP | 2015-230280 | 12/2015 |

OTHER PUBLICATIONS

Wilhelm et al., "Perspectives of upconverting luminescent nanoparticles for (bio)-analytical applications" Doctoral Thesis, (2014). https://epub.uni-regensburg.de/30447/1/Dissertation_Stefan_WILHELM.pdf (Year: 2014).*
Juntunen, E. et al., "Effects of blood sample anticoagulants on lateral flow assays using luminescent photon-upconverting and Eu(III) nanoparticle reporters", Analytical Biochemistry, 492; pp. 13-20, 2016.
Juntunen, E., "Lateral Flow Immunoassays with Fluorescent Reporter Technologies", Thesis, University of Turku, Jan. 2018.
Liu, C. et al., "Upconversion luminescence nanoparticles-based lateral flow immunochromatographic assay for cephalexin detection", Journal of Materials Chemistry C, 2(45); pp. 9637-9642, 2014.
Sedlmeier, A et al., "Highly Sensitive Laser Scanning of Photon-Upconverting Nanoparticles on a Macroscopic Scale", Analytical Chemistry, 88; pp. 1835-1841, 2016.
Supporting information for Hao, H. et al., "Quantitative Lateral Flow Strip Sensor Using Highly Doped Upconversion Nanoparticles", Analytical Chemistry, 90(21); pp. 12356-12360, 2018.
Wilhelm, S. et al., "Water dispersible upconverting nanoparticles: effects of surface modification on their luminescence and colloidal stability", Nanoscale, 7; pp. 1403-1410, 2015.
Extended European Search Report issued in Corresponding European Application No. 19866629.9, dated Jun. 3, 2022.
He et al., "Quantitative Lateral Flow Strip Sensor Using Highly Doped Upconversion Nanoparticles" Analytical Chemistry 2018, 90, 12356-12360.
Liang et al., "Upconversion Nanocrystals Mediated Lateral-Flow Nanoplatform for in Vitro Detection" Applied Materials & Interfaces 2017, 9(4), 3497-3504.
Zhao et al., "Upconversion fluorescent strip sensor for rapid determination of Vibrio anguillarum" Nanoscale 2014, 6(7), 3804-3809.
International Preliminary Report on Patentability, PCT/AU2019/051034, report completion date Jan. 14, 2021, 19 pages.
International Search Report, PCT/AU2019/051034, report completion date Nov. 25, 2019, 2 pages.
Written Opinion of the International Searching Authority, PCT/AU2019/051034, report completion date Nov. 25, 2019, 4 pages.
"Synthesis and Application of Rare Earth Upconversion Luminescent Nanomaterials," Wang Meng, Ed., Shenyang: Northeastern University Press, Apr. 2015, ISBN 978-7-5517-0953-8, with Machine translation.
Chenshuo Ma et al., "Optimal Sensitizer Concentration in Single Upconversion Nanocrystals," Nano Letters, vol. 17, No. 5. p. 2858-2864, Apr. 24, 2017.

* cited by examiner

*Primary Examiner* — Elizabeth C. Kemmerer
*Assistant Examiner* — Mckenzie A Dunn
(74) *Attorney, Agent, or Firm* — Norton Rose Fulbright US LLP

(57) ABSTRACT

The present invention relates to methods for determining the quantity of an analyte in sample using lateral flow strips comprising highly-doped upconversion nanoparticles.

19 Claims, 8 Drawing Sheets

ANALYTE QUANTITATION

CROSS-REFERENCE TO RELATED APPLICATIONS

The present application is a U.S. National Stage patent application of International Patent Application No. PCT/AU2019/051034, filed on Sep. 25, 2019 which claims priority to AU 2018903614, filed on Sep. 25, 2018, the benefit of which is claimed and the disclosures of which are incorporated herein by reference in their entireties.

FIELD OF THE DISCLOSURE

The present invention relates to methods for determining the quantity of an analyte in sample using lateral flow strips comprising highly-doped upconversion nanoparticles.

BACKGROUND OF THE DISCLOSURE

Any discussion of the prior art throughout the specification should in no way be considered as an admission that such prior art is widely known or forms part of the common general knowledge in the field.

Lateral flow strips are a promising technology for detecting and quantitating analytes, such as biomarkers in a sample. Paper-based lateral flow strips are generally inexpensive, but current assay techniques do not provide sufficient sensitivity for the detection and quantitation of analytes present in low concentrations, for example biomarkers used for early stage cancer diagnosis. A number of attempts have been made to improve known assay techniques, however, such attempts have largely been unsuccessful.

In this context, there is a need for improved assays based on lateral flow strips that are capable of detecting and quantitating analytes present in samples at low concentrations.

SUMMARY OF THE DISCLOSURE

In one aspect of the present disclosure there is provided a method for determining the quantity of at least one analyte in a sample, the method comprising:
providing a lateral flow strip comprising a capture moiety and a conjugate comprising a detection moiety capable of binding the at least one analyte and highly-doped upconversion nanoparticles for visualising interaction of the at least one analyte and the capture moiety;
applying the sample to the lateral flow strip such that the conjugate binds the analyte to provide a bound analyte that is subsequently captured by the capture moiety;
providing a testing device comprising an excitation light source configured to elicit a detectable signal from the highly-doped upconversion nanoparticles and a detector to capture the detectable signal, the testing device being capable of receiving the lateral flow strip;
inserting the lateral flow strip to which the sample has been applied into the testing device;
irradiating an area of the lateral flow strip comprising the highly-doped upconversion nanoparticles with a beam of light so as to elicit a detectable signal from the highly-doped upconversion nanoparticles; and
detecting the detectable signal and determining the quantity of the at least one analyte in the sample based on the detectable signal.

The highly-doped upconversion nanoparticles may have a size between about 10 nm and about 200 nm.

The highly-doped upconversion nanoparticles may have a size of about 50 nm.

The highly-doped upconversion nanoparticles may be inert shell passivated.

The capture moiety and/or the detection moiety may include one or more of: an antibody, an aptamer, an epitope, a nucleic acid or a molecular imprinted polymer.

The area irradiated may be between about 1 $\mu m^2$ and about 10000000 $\mu m^2$.

The testing device may further comprise a lens or an array of lenses interposed between the excitation light source and the lateral flow strip so to focus the beam of light on the lateral flow strip.

The testing device may further comprise a lens or an array of lenses interposed between the lateral flow strip and the detector so as to focus the signal on the detector.

The lens may be a hemisphere lens.

The testing device may further comprise a short pass filter, a long pass filter or a bandpass filter to minimise or prevent laser scattering.

The filter may be in the form of heat-absorbing glass, for example KG-3 heat-absorbing glass.

The detector may be a camera, such as for example a smart phone camera.

The detector may be a single element detector, such as for example a photon diode.

The detectable signal may be visible light or infrared light.

The excitation light source may be a laser diode or a near IR light source, such as an LED near IR light source.

The laser diode may be a 980 nm 300 mw laser diode, a 790 nm 100 mw laser diode, or a 1550 nm 100 mw laser diode.

The beam of light may have a power density of at least about 0.001 $MW/cm^2$, or at least about 0.01 $MW/cm^2$, or at least about 0.05 $MW/cm^2$, or at least about 0.1 $MW/cm^2$, or at least about 0.5 $MW/cm^2$, or at least about 1.0 $MW/cm^2$, or at least about 1.5 $MW/cm^2$.

The beam of light may have a power density between about 0.001 $MW/cm^2$ and about 1.5 $MW/cm^2$, or between about 0.01 $MW/cm^2$ and about 1.5 $MW/cm^2$.

The sample may be a biological sample.

The sample may be a bodily fluid, such as for example, urine, sweat, blood or saliva.

The sample may be a liquid sample or gas sample.

The gas sample may be breath.

The analyte may be a biomarker.

The analyte may be a biomarker used for cancer diagnosis or evaluation of cardiac function.

The analyte may be estrogen receptor, progesterone receptor, PSA, EphA2, HER-2 protein, EGFR, KRAS, UGT1A1, EML4, AL, TGF-β, IDH1, AFP, CEA, BCR-ABL, CEBPA, FLT3, KIT, NPM1, PML-RARα, CD20, JAK2, CD25, BRAF, NMP22, CA-125, HE4, HGF, CK-MB, LDH, AST, Mb, IMA, BNP or MET, or any combination thereof.

The method may comprise determining the quantity of a plurality of analytes.

The lateral flow strip may be a paper-based lateral flow strip or a microfluidic device.

The testing device may comprise a plastic housing.

The plastic housing may be produced by 3D printing.

The quantity of the at least one analyte in the sample may be determined by fitting intensity of an image captured by the detector with a pre-set intensity-concentration curve for the analyte.

DETAILED DESCRIPTION

Figure 1:
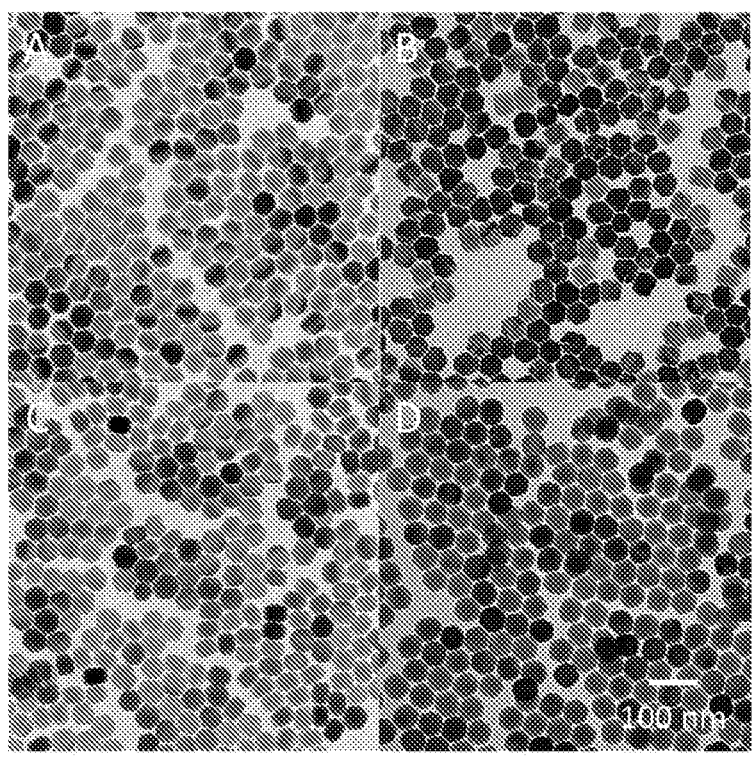
FIG. 1: TEM photos of A) 2% Er/20% Yb UCNPs, B) 8% Er/60% Yb@NaYF$_4$ UCNPs, C) 0.5% Tm/20% Yb UCNPs, and D) 8% Tm/60% Yb@NaYF$_4$ UCNPs. Scale bar: 100 nm.

The terms "comprise", "comprises", "comprised" or "comprising", "including" or "having" and the like in the present specification and claims are used in an inclusive sense, i.e., to specify the presence of the stated features but not preclude the presence of additional or further features.

The term "about" is understood to refer to a range of +/−10%, preferably +/−5% or +/−1% or, more preferably, +/−0.1%.

According to the present disclosure, there is provided a method for determining the quantity of at least one analyte in a sample, the method comprising:

providing a lateral flow strip comprising a capture moiety and a conjugate comprising a detection moiety capable of binding the at least one analyte and highly-doped upconversion nanoparticles for visualising interaction of the at least one analyte and the capture moiety;

applying the sample to the lateral flow strip such that the conjugate binds the analyte to provide a bound analyte that is subsequently captured by the capture moiety;

providing a testing device comprising an excitation light source configured to elicit a detectable signal from the highly-doped upconversion nanoparticles and a detector to capture the detectable signal, the testing device being capable of receiving the lateral flow strip;

inserting the lateral flow strip to which the sample has been applied into the testing device;

irradiating an area of the lateral flow strip comprising the highly-doped upconversion nanoparticles with a beam of light so as to elicit a detectable signal from the highly-doped upconversion nanoparticles; and detecting the detectable signal and determining the quantity of the at least one analyte in the sample based on the detectable signal.

The method is based on the use of a focused beam of light that activates highly-doped upconversion nanoparticles present on a lateral flow strip to produce very bright emissions. The brightness of the emissions opens the way for ultra-sensitive detection and quantitation of analytes present in very low abundance.

The methods described herein enable rapid, quantitative and low-cost analysis of analytes present in a range of samples and are particularly well suited to point-of-care testing applications, and in particular diagnostics. In some embodiments the method may be used in the detection and quantitation of biomarkers used for early stage diagnosis of diseases such as cancer. The inventors have shown that biomarkers present in pg/mL quantities are able to be successfully detected and quantified using the present method.

Lateral flow test strips have been used for many years in the detection of analytes in fields including biomedicine, agriculture, food and environmental sciences and can take a number of different forms. In one type, the test strip is divided into four domains, which can be made of a single kind of material or several different kinds of material (for example, up to four different kinds of materials). The first domain is for sample addition. This domain functions to remove any viscous or particulate materials that may be present in the sample and also to condition the sample for reactions that occur in the following domains. The second domain is a mobile phase with a colour conjugate made from conjugation between a visible colour marker (for example coloured beads, colloidal gold, fluorescent dyes, etc.) and a detection moiety, such as an antibody. The detection moiety is capable of binding a specific analyte in the sample (such as an antigen) and forms an analyte-colour conjugate complex. The third domain is a solid-phase with an immobilized capture moiety. The capture moiety can bind the analyte of the analyte-colour conjugate complex to form a captured capture moiety-analyte-color conjugate complex sandwich. The fourth domain is for solution absorption and draws the sample solution towards it continuously.

Lateral flow strips suitable for use in the present method may be prepared by standard methods known to those skilled in the art. The lateral flow strip includes a conjugate comprising a detection moiety (such as for example an antibody) that is capable of binding the at least one analyte (such as for example an antigen) and highly-doped upconversion nanoparticles. The lateral flow strip also includes a capture moiety which serves to immobilize the conjugate on the lateral flow strip via interaction with the analyte once it is bound to the conjugate. The presence of the analyte is then detected using emission from the highly-doped upconversion nanoparticles. Typically, the lateral flow strip is a paper-based lateral flow strip.

Lateral flow strips may be adapted for assaying a range of different analyte types. For example, lateral flow strips may be used for biomarker testing, blood glucose testing, metabolic testing (such as thyroid stimulating hormone), blood gas and electrolyte analysis, rapid coagulation testing, rapid cardiac marker diagnostics, drugs of abuse screening, urine testing, pregnancy testing, fecal occult blood analysis, food pathogen screening, complete blood count, hemoglobin diagnostics, infectious disease testing (e.g., a multi-analyte rapid diagnostic test for detecting malaria infection), cholesterol screening and hormone testing.

In some embodiments the analyte may be a biomarker. A biomarker may be a drug or drug metabolite, an antibody or antibody fragment, a hapten, a protein or peptide, an amino acid, a receptor, a steroid, a vitamin, an antibiotic, a sugar, a hormone, an antigen, a nucleic acid such as RNA or DNA, a carbohydrate, a glycoprotein, a lipid, a polysaccharide, a proteoglycan, a tissue-specific marker, a cell or cell type-specific marker, a metabolite, a virus or a viral marker, a bacterium or a bacterial marker, a fungus or a fungal marker, a toxin, an allergen etc.

In some embodiments the biomarker is a biomarker used for cancer diagnosis or evaluation of cardiac function.

In some embodiments the biomarker may be, for example, an estrogen receptor (ER), progesterone receptor (PR), PSA, EphA2, HER-2 protein, EGFR, KRAS, UGT1A1, EML4, AL IDH1, AFP, CEA, BCR-ABL, CEBPA, FLT3, KIT, NPM1, PML-RARα, CD20, JAK2, CD25, BRAF, NMP22, CA-125, HE4, HGF, CK-MB, LDH, TGF-β AST, Mb, IMA, BNP or MET.

Appropriate capture and detection moieties may be selected based on the analyte or analytes that are to be quantified. In some embodiments the capture and detection moieties are antibodies, aptamers, epitopes, nucleic acids and/or molecular imprinted polymers.

Figure 5:
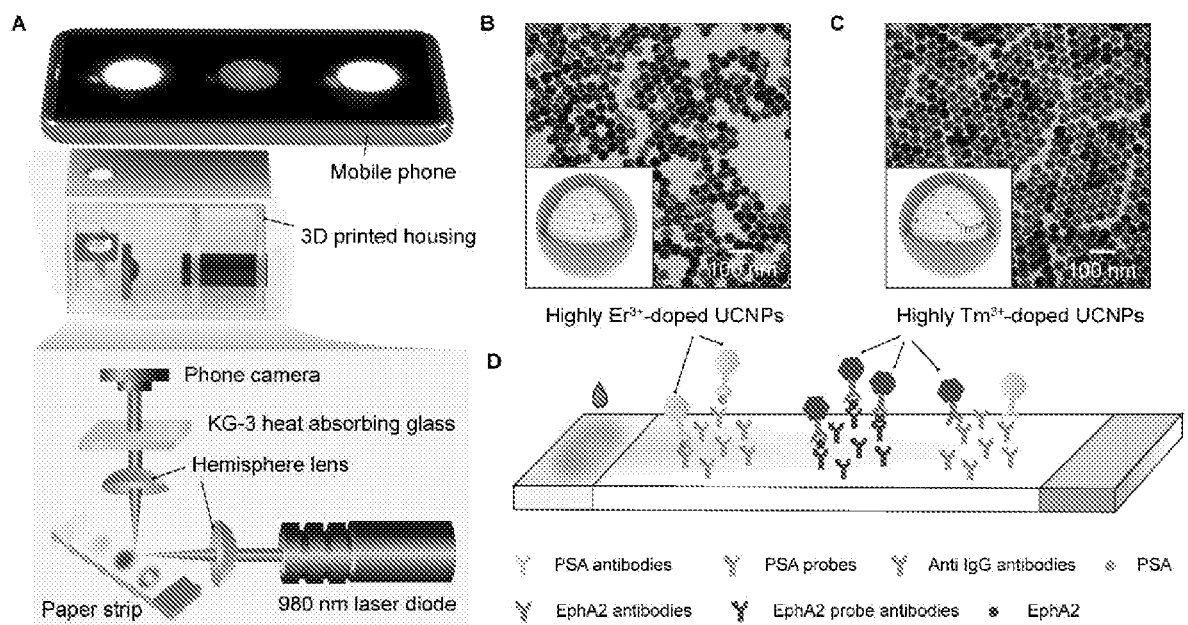
FIG. 5: A) Schematic illustration of a mobile phone based reader with optics layout. B) Structure of highly Er$^{3+}$ doped core-shell UCNPs with the corresponding TEM image. C) Structure of highly Tm$^{3+}$ doped core-shell UCNPs with the corresponding TEM image. D) Two-colour LFS assays for PSA and EphA2 analytes.

In some embodiments the lateral flow strips may be adapted for detection of a plurality of analytes in a single sample. This may be achieved by including multiple conjugates having detection moieties for the different analytes and corresponding multiple capture moieties. Each conjugate includes different highly-doped upconversion nanoparticles that emit different colours. FIG. 5 shows a lateral flow strip adapted for detecting and quantitating PSA and EphA2 simultaneously in a multiplexed assay. Detecting and quantitating multiple analytes in a single sample may be of particular interest in early cancer diagnosis where it is useful to test for the presence of a plurality of biomarkers which are indicative of malignant cells.

Typically the sample is a biological sample. In some embodiments the sample is a bodily fluid, such as urine, sweat, blood, bile, blood plasma, blood serum, breast milk, saliva, cerebrospinal fluid, lymph, sputum, synovial fluid, tears, peritoneal fluid, pleural fluid, mucus or any combination thereof. The sample may be applied to the lateral flow strip in the form of a liquid, but alternatively may be applied as a gas. The gas may be breath.

The highly-doped upconversion nanoparticles may comprise a host material, a sensitiser and an activator.

The highly-doped upconversion nanoparticles may have an activator concentration of at least about 2.5 mol %, at least about 3 mol %, at least about 4 mol %, at least about 5 mol %, at least about 6 mol %, at least about 7 mol %, at least about 8 mol %, at least about 9 mol %, at least about 10 mol %, at least about 11 mol %, at least about 12 mol %, at least about 13 mol %, at least about 14 mol %, at least about 15 mol %, at least about 16 mol %, at least about 17 mol %, at least about 18 mol %, at least about 19 mol %, at least about 20 mol %, at least about 25 mol %, at least about 30 mol %, at least about 35 mol %, at least about 40 mol %, or at least about 50%.

The highly-doped upconversion nanoparticles may have an activator concentration between about 2.5 mol % and about 75 mol %, or between about 2.5 mol % and about 70 mol %, or between about 2.5 mol %, and about 65 mol %, or between about 2.5 mol % and about 60 mol %, or between about 2.5 mol % and about 55 mol % or between about 2.5 mol % and about 50 mol %, or between about 2.5 mol % and about 45 mol %, or between about 2.5 mol % and about 40 mol %, or between about 2.5 mol % and about 35 mol %, or between about 2.5 mol % and about 30 mol %, or between about 2.5 mol % and about 25 mol %, or between about 2.5 mol % and about 20 mol %, or between about 2.5 mol % and about 15 mol %, or between about 2.5 mol % and about 10 mol %, or between about 3 mol % and about 75 mol %, or between about 3 mol % and about 70 mol %, or between about 3 mol % and about 65 mol %, or between about 3 mol % and about 60 mol %, or between about 3 mol % and about 55 mol % or between about 3 mol % and about 50 mol %, or between about 3 mol % and about 45 mol %, or between about 3 mol % and about 40 mol %, or between about 3 mol % and about 35 mol %, or between about 3 mol % and about 30 mol %, or between about 3 mol %, and about 25 mol %, or between about 3 mol % and about 20 mol %, or between about 3 mol % and about 15 mol %, or between about 3 mol % and about 10 mol %, or between about 4 mol % and about 75 mol %, or between about 4 mol % and about 70 mol %, or between about 4 mol % and about 65 mol %, or between about 4 mol % and about 60 mol %, or between about 4 mol % and about 55 mol % or between about 4 mol % and about 50 mol %, or between about 4 mol % and about 45 mol %, or between about 4 mol % and about 40 mol %, or between about 4 mol % and about 35 mol %, or between about 4 mol % and about 30 mol %, or between about 4 mol % and about 25 mol %, or between about 4 mol % and about 20 mol %, or between about 4 mol % and about 15 mol %, or between about 4 mol % and about 10 mol %, or between about 6 mol % and about 75 mol %, or between about 6 mol % and about 70 mol %, or between about 6 mol % and about 65 mol %, or between about 6 mol % and about 60 mol %, or between about 6 mol % and about 55 mol % or between about 6 mol % and about 50 mol %, or between about 6 mol % and about 45 mol %, or between about 6 mol % and about 40 mol %, or between about 6 mol % and about 35 mol %, or between about 6 mol % and about 30 mol %, or between about 6 mol % and about 25 mol %, or between about 6 mol % and about 20 mol %, or between about 6 mol % and about 15 mol %, or between about 6 mol % and about 10 mol %, or between about 8 mol % and about 75 mol %, or between about 8 mol % and about 70 mol %, or between about 8 mol % and about 65 mol %, or between about 8 mol % and about 60 mol %, or between about 8 mol % and about 55 mol % or between about 8 mol % and about 50 mol %, or between about 8 mol % and about 45 mol %, or between about 8 mol % and about 40 mol %, or between about 8 mol % and about 35 mol %, or between about 8 mol % and about 30 mol %, or between about 8 mol % and about 25 mol %, or between about 8 mol % and about 20 mol %, or between about 8 mol % and about 15 mol %, or between about 8 mol % and about 10 mol %, or about 8 mol %.

The highly-doped upconversion nanoparticles may have a sensitiser concentration of at least about 25 mol %, at least about 26 mol %, at least about 27 mol %, at least about 28 mol %, at least about 29 mol %, at least about 30 mol %, at least about 31 mol %, at least about 32 mol %, at least about 33 mol %, at least about 34 mol %, at least about 35 mol %, at least about 36 mol %, at least about 37 mol %, at least about 38 mol %, at least about 39 mol %, at least about 40 mol %, at least about 41 mol %, at least about 42 mol %, at least about 43 mol %, at least about 44 mol %, at least about 45 mol %, at least about 46 mol %, at least about 47 mol %, at least about 48 mol %, at least about 49 mol %, at least about 50 mol %, at least about 51 mol %, at least about 52 mol %, at least about 53 mol %, at least about 54 mol %, at least about 55 mol %, at least about 56 mol %, at least about 57 mol %, at least about 58 mol %, at least about 59 mol %, at least about 60 mol %, at least about 61 mol %, at least about 62 mol %, at least about 63 mol %, at least about 64 mol %, at least about 65 mol %, at least about 66 mol %, at least about 67 mol %, at least about 68 mol %, at least about 69 mol %, at least about 70 mol %, at least about 71 mol %, at least about 72 mol %, at least about 73 mol %, at least about 74 mol %, at least about 75 mol %, at least about 80 mol % or at least about 85 mol %.

The highly-doped upconversion nanoparticles may have a sensitiser concentration between about 25 mol % and about 90 mol %, or between about 25 mol % and about 85 mol %, or between about 25 mol % and about 80 mol %, or between about 25 mol % and about 75 mol %, or between about 25 mol % and about 65 mol %, or between about 30 mol % and about 90 mol %, or between about 30 mol % and about 85 mol %, or between about 30 mol % and about 80 mol %, or between about 30 mol % and about 75 mol %, or between about 30 mol % and about 65 mol %, or between about 35 mol % and about 90 mol %, or between about 35 mol % and about 85 mol %, or between about 35 mol % and about 80 mol %, or between about 35 mol % and about 75 mol %, or between about 35 mol % and about 65 mol %, or between about 40 mol % and about 90 mol %, or between about 40 mol % and about 85 mol %, or between about 40 mol % and about 80 mol %, or between about 40 mol % and about 75 mol %, or between about 40 mol % and about 65 mol %, or between about 45 mol % and about 90 mol %, or between about 45 mol % and about 85 mol %, or between about 45 mol % and about 80 mol %, or between about 45 mol % and about 75 mol %, or between about 45 mol % and about 65 mol %, or between about 50 mol % and about 90 mol %, or between about 50 mol % and about 85 mol %, or between about 50 mol % and about 80 mol %, or between about 50 mol % and about 75 mol %, or between about 50 mol % and about 65 mol %, or between about 55 mol % and about 90 mol %, or between about 55 mol % and about 85 mol %, or between about 55 mol % and about 80 mol %, or between about 55 mol % and about 75 mol %, or between about 55 mol % and about 65 mol %, or between about 60 mol % and about 95 mol %, or between about 60 mol % and about 90 mol %, or between about 60 mol % and about 85 mol %, or between about 60 mol % and about 80 mol %, or between about 60 mol % and about 70 mol %, or about 60 mol %.

The activator and sensitiser in the highly-doped upconversion nanoparticles may be present in any and all combinations of the above concentrations.

The activator may be $Yb^{3+}$, $Er^{3+}$, $Tm^{3+}$, $Sm^{3+}$, $Dy^{3+}$, $Ho^{3+}$, $Eu^{3+}$, $Tb^{3+}$ or $Pr^{3+}$ including combinations thereof. In one embodiment, the activator is $Er^{3+}$ or $Tm^{3+}$.

The sensitiser may be $Yb^{3+}$, $Nd^{3+}$, $Gd^{3+}$ or $Ce^{3+}$, including combinations thereof. In one embodiment, the sensitiser is $Yb^{3+}$.

The host material may be an alkali fluoride, an oxide or an oxysulfide. Suitable host materials include, but are not limited to, alkali fluorides, such as $NaGdF_4$, $Ca_2F$, $NaYF_4$, $LiYF_4$, $NaLuF_4$ and $LiLuF_4$, $KMnF_3$, and oxides, such as $Y_2O_3$. Mixtures of these materials are also contemplated. In one embodiment, the host material is $NaYF_4$. Where the particles are crystalline the $NaYF_4$ may be hexagonal phase, or any other crystal phase.

In other embodiments the sensitiser, activator and host material are protected against surface quenchers by a shell, such that the highly-doped upconversion nanoparticles are core-shell particles wherein the core comprises the activator, the sensitiser and the host material, and the shell comprises, or consists of, a material which prevents, retards or inhibits surface quenching. The shell may partially or completely encapsulate the core. Preferably, the shell comprises or consists of the same material as the host material, but without the rare-earth metal dopants. In the case of crystals, this avoids the need for phase matching.

In alternative embodiments the highly-doped upconversion nanoparticles may omit a sensitiser and hence comprise a host material and an activator.

The highly-doped upconversion nanoparticles may have a size between about 10 nm and about 200 nm, or a size between about 10 nm and about 175 nm, or a size between about 10 nm and about 165 nm, or a size between about 10 nm and about 155 nm, or a size between about 10 nm and about 145 nm, or a size between about 10 nm and about 135 nm, or a size between about 10 nm and about 125 nm, or a size between about 10 nm and about 115 nm, or a size between about 10 nm and about 105 nm, or a size between about 10 nm and about 100 nm, or a size between about 10 nm and about 95 nm, or a size between about 10 nm and about 85 nm, or a size between about 10 nm and about 75 nm, or a size between about 10 nm and about 65 nm, or a size between about 20 nm and about 160 nm, or a size between about 20 nm and about 150 nm, or a size between about 20 nm and about 140 nm, or a size between about 20 nm and about 130 nm, or a size between about 20 nm and about 120 nm, or a size between about 20 nm and about 110 nm, or a size between about 20 nm and about 100 nm, or a size between about 20 nm and about 90 nm, or a size between about 20 nm and about 80 nm, or a size between about 20 nm and about 70 nm, or a size between about 30 nm and about 160 nm, or a size between about 30 nm and about 150 nm, or a size between about 30 nm and about 140 nm, or a size between about 30 nm and about 130 nm, or a size between about 30 nm and about 120 nm, or a size between about 30 nm and about 110 nm, or a size between about 30 nm and about 100 nm, or a size between about 20 nm and about 75 nm, or a size between about 25 nm and about 70 nm, or a size between about 30 nm and about 60 nm, or a size between about 40 nm and about 60 nm, or a size of about 50 nm.

In some embodiments the highly-doped upconversion nanoparticles are 8% Er/60% Yb@$NaYF_4$, 8% Tm/60% Yb@$NaYF_4$, 40% Er/60Yb@$NaYF_4$ or 100% Er@$NaYF_4$.

The method also includes provision of a testing device for the lateral flow strip. The testing device includes the excitation light source, which produces a beam of light so as to elicit a detectable signal from the highly-doped upconversion nanoparticles, and may include collection optics for focusing the beam and the detectable signal. The excitation light source may be any light source that is capable of eliciting a detectable signal from the highly-doped upconversion nanoparticles. In some embodiments the excitation light source is a laser diode or near IR light source, such as an LED near IR light source. The detectable signal may be visible light or infrared light.

The testing device may be adapted for use with a detector, such as for example a camera or a single element detector. In some embodiments the detector is a smart phone camera.

The beam of light may have a power density of at least about 0.001 MW/cm$^2$, or at least about 0.01 MW/cm$^2$, or at least about 0.05 MW/cm$^2$, or at least about 0.1 MW/cm$^2$, or at least about 0.5 MW/cm$^2$, or at least about 1.0 MW/cm$^2$, or at least about 1.5 MW/cm$^2$. In some embodiments the beam of light has a power density between about 0.001 MW/cm$^2$ and about 1.5 MW/cm$^2$, or between about 0.01 MW/cm$^2$ and about 1.5 MW/cm$^2$.

In some embodiments the area irradiated may be between about 1 µm$^2$ and about 10000000 µm$^2$, or between about 1 µm$^2$ and about 1000000 µm$^2$, or between about 1 µm$^2$ and about 100000 µm$^2$, or between about 1 µm$^2$ and about 10000 µm$^2$, or between about 1 µm$^2$ and about 10000 µm$^2$, or between about 1 µm$^2$ and about 1000 µm$^2$, or between about 1 µm$^2$ and about 100 µm$^2$. Irradiation of a small area of the lateral flow strip may serve to minimise light scattering and/or auto-fluorescence and therefore optimise sensitivity when analysing small sample volumes.

FIG. 5 shows a testing device in accordance with one embodiment of the invention. In this embodiment a 3D-printed plastic housing is provided which encloses a low-cost 980 nm laser diode and collection optics. The collection optics include a pair of hemisphere lenses, one interposed between the laser diode and the lateral flow strip, and the other interposed between the lateral flow strip and the detector. Also included is KG-3 heat absorbing glass which acts as a short pass filter to remove laser scattering. The housing may also include an aperture (not shown) through which the lateral flow strip can be inserted. Conveniently, this testing device can be produced for less than A$100. A smart phone is used as the detector as the emission from the highly-doped upconversion nanoparticles is of sufficient brightness to be detected by a camera. As such, a costly single photon counting detector is not required which substantially lowers the cost a simplicity of performing the method.

The quantity of the at least one analyte in the sample may be determined by fitting the intensity of the image captured by the detector with a pre-set intensity-concentration curve for the analyte. Videos of a series of images that record the strength of the detectable signal over the testing area, background area and control area may be transferred from the smartphone to a computer for further analysis using MATLAB software. The intensity of each image is calculated by summing the intensities of each pixel from the corresponding colour channel which is then further averaged from at least three frames in that group. This data analysis process may be programmed into an app so that the smartphones can directly report analyte concentration based on the intensity of each image.

EXAMPLES

In the following examples, upconversion nanoparticles (UCNPs) highly-doped with Er$^{3+}$ ions to emit yellowish upconversion emissions and Tm$^{3+}$ ions to emit purple upconversion emissions were applied as multi-colour reporters in lateral flow strips (LPS). A plastic holder was printed which aligns a low-cost excitation laser diode and collection optics. It will be appreciated that the excitation beam can be tightly focussed to specifically illuminate a small region on the paper substrate, which unlocks the brightness of the highly doped UCNPs, enabling them to deliver high sensitivity detection using small samples volumes. As demonstrated below, highly doped UCNPs provide significantly higher brightness compared to conventional UCNPs, allowing sensitive detection in a quantitative, multiplexed assay without crosstalk.

1. Synthesis of UCNPs

NaYF$_4$: Yb$^{3+}$, Er$^{3+}$/Tm$^{3+}$ nanocrystals with different levels of doping (2% Er/20% Yb, 8% Er/60% Yb, 0.5% Tm/20% Yb and 8% Tm/60% Yb) were synthesized as described in Jin et al. Nature Communications 2018, 9 3290. In a typical experiment, 1 mmol RECl$_3$.6H$_2$O (RE=Y, Yb, Tm) with the desired molar ratio was added to a flask containing 6 mL OA and 15 mL ODE. The mixture was heated to 160° C. under argon flow for 30 min to obtain a clear solution and then cooled to about 50° C. 5 mL methanol solution of NH$_4$F (4 mmol) and NaOH (2.5 mmol) was then added and the solution was stirred for 30 min. The mixture was heated to 150° C. under argon flow for 20 min to expel methanol, and then further heated to 310° C. for another 90 min, Finally, the reaction solution was cooled to room temperature. The products were precipitated using ethanol, centrifuged at 9000 rpm for 5 min, and washed 3 times with cyclohexane, ethanol and methanol to obtain the nanoparticles.

Layer-by-layer epitaxial growth was employed to produce nanoparticles having a core-shell structure. The procedure for preparing shell precursors is similar to the procedure used in respect of the core nanoparticles, until the step where the reaction solution is slowly heated to 150° C. and kept for 20 min. Instead of further heating to 300° C. to trigger nanocrystal growth, the solution was cooled to room temperature. Under those conditions, the shell precursors were produced. For epitaxial growth, 0.15 mmol of as-prepared core nanocrystals were added to 6 ml OA and 6 ml ODE. The mixture was heated to 170° C. under argon for 30 min, and then further heated to 300° C. Next, 0.25 ml of as-prepared shell precursors were injected into the reaction mixture and ripened at 300° C. for 4 min. The same injection and ripening cycles were performed several times to obtain nanocrystals having the desired size. Finally, the slurry was cooled to room temperature and the formed nanocrystals were purified using the same procedure as was used to obtain the core nanocrystals.

2. Bioconjugation of UCNPs with Antibodies

Ligand exchange was used to convert OA-capped UCNPs to cPEG-(polyethylene glycol modified with a carboxy group) coated products. 1.5 mL of 20 mg/mL UCNPs in cyclohexane were precipitated using ethanol, and after centrifugation, the UCNPs were redispersed in 3 mL THF by vortexing and sonication. 1.5 mL of 200 mg cPEG in THF solution was then added, and the mixed solution was stirred at room temperature for 24 h. 3 mL of MiliQ water was then added and mixed with shaking. The solution was then extracted using 1 mL of hexane to remove the OA molecules. After removing the oil phase, the solution was placed in vacuo overnight to evaporate organic solvents. The solution was then dialyzed in 1 L of MiliQ water for 24 h to remove excess PEG.

After converting, the cPEG-UCNPs were changed into MES buffer (pH 4.5) using centrifugation to a final concentration of 1 mg/mL. 10 µL of cPEG-UCNPs, 100 µg EDC and 100 µg NHS were mixed in 90 µL MES buffer (pH 4.5). After 2 h of gentle shaking, the sample was washed with the MES buffer twice (centrifuged at 14,000 rpm for 20 min). After the final centrifugation step, the precipitate was suspended in 50 μL MES buffer. The solution was then mixed with 50 μL of IgG antibody (0.1 mg/mL anti-PSA monoclonal antibody produced in rabbit/anti-EphA2 monoclonal antibody produced in rabbit; Sigma) and incubated in a 37° C. shaker overnight. After twice washing with MES buffer (centrifuges at 14,000 rpm for 20 min), the sample was suspended in 100 μL of MES buffer and sonicated for 5 s.

3. TEM Characterisation

2% Er/20% Yb, 8% Er/60% Yb@NaYF$_4$, 0.5% Tm/20% Yb and 8% Tm/60% Yb@NaYF$_4$ UCNPs were characterised by transmission electron microscopy. As shown in FIG. 1, the UCNPs were highly uniform.

4. UV Absorption Spectrum and Dynamic Light Scattering

Figure 2:
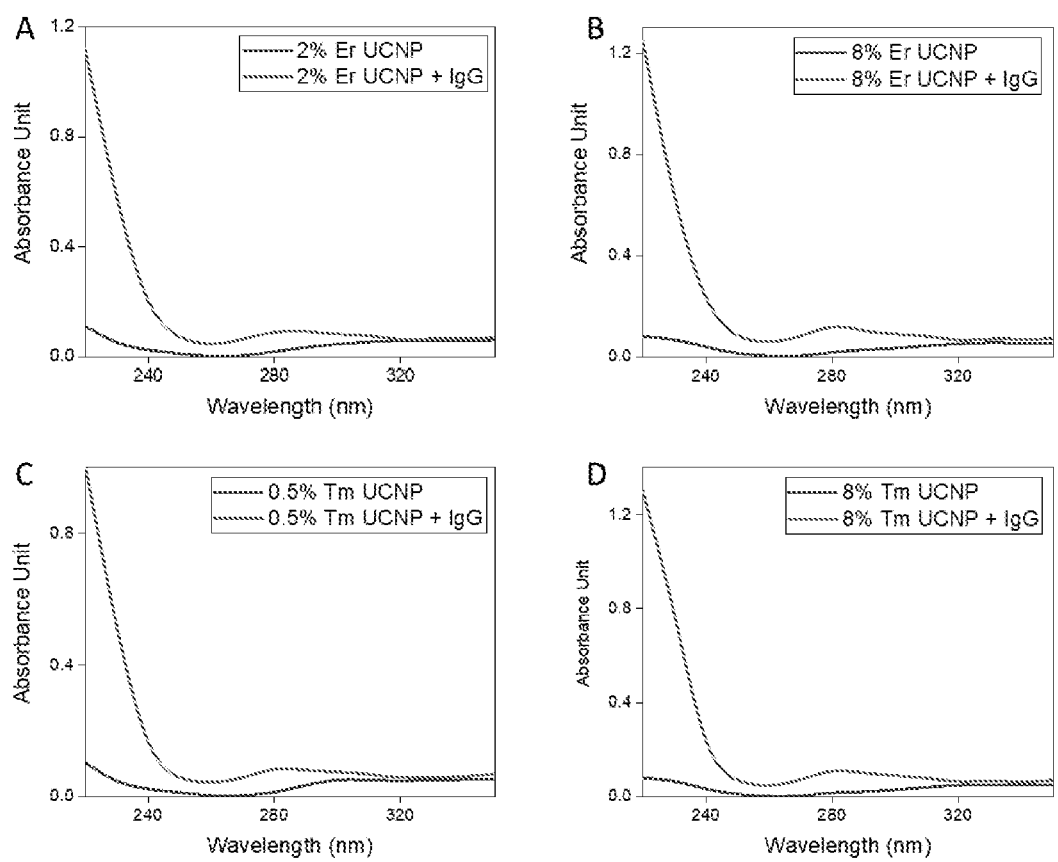
FIG. 2: UV absorption spectrum of cPEG-coated and IgG-modified UCNPs. A) 2% Er/20% Yb B) 8% Er/60% Yb@NaYF$_4$ C) 0.5% Tm/20% Yb and D) 8% Tm/60% Yb@NaY F$_4$.

A Nanodrop2000 was used to determine the UV absorption spectrum of the cPEG-coated UCNPs and the IgG-conjugated UCNPs to confirm that the antibodies were conjugated to the surface of UCNPs (FIG. 2).

Dynamic light scattering (DLS) was used to determine the size distribution of each sample in the MES buffer (pH 6.8). The results also confirmed the presence of IgG on UCNPs surfaces (Table 1).

TABLE 1

|  | cPEG-UCNP | IgG-cPEG-UCNP |
| --- | --- | --- |
| 2% Er/20% Yb | 50.6 nm | 64.4 nm |
| 8% Er/60% Yb | 58.1 nm | 75.1 nm |
| 0.5% Tm/20% Yb | 52.4 nm | 66.8 nm |
| 8% Tm/60% Yb | 60.4 nm | 76.2 nm |

5. Power Dependent Spectra

Figure 3:
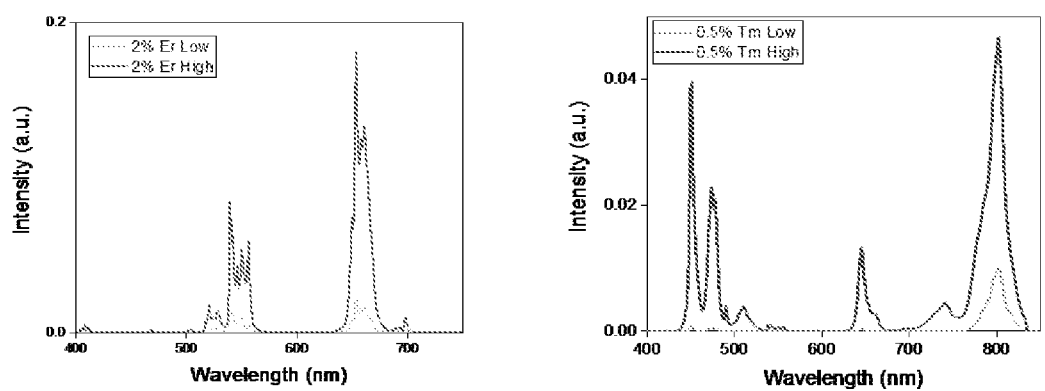
FIG. 3: Power dependent spectra of 2% Er/20% Yb (left) and 0.5% Tm/20% Yb (right) under low and high excitation power.

Power dependent spectra were determined for 2% Er/20% Yb and 0.5% Tm/20% Yb under low and high excitation power. The results are presented in FIG. 3.

6. Fabrication of Paper Based Strip

The strip structure comprises an adhesive PVC back pad, a nitrocellulose membrane (FF120HP membrane, GE Life Science), a sample pad (CF4, GE Life Science) and an absorbent pad (CFS, GE Life Science). The sample pad, nitrocellulose membrane and absorbent pad were mounted onto the PVC back pad with 2 mm overlap. The assembled pads were cut into strips having a width of 3 mm. Test area and control area were separately coated with 0.5 μL of 0.2 mg/mL anti-PSA/EphA2 polyclonal antibodies produced in mouse (Sigma) and 0.5 μL of 2 mg/mL anti-rabbit IgG antibodies (Sigma) and incubated overnight at below 4° C.

7. Lateral Flow Strip target Detection Assay

UCNP reporters were transferred to a working buffer (pH 6.8 MES buffer, 0.5% w/v tween 20, 1% w/v BSA). After mixing, sample solutions with UCNP reporters were applied to the sample pad of the strip. After 10 mins, washing buffer (pH 6.8 MES buffer, 0.5% w/v tween 20) was added to the sample pad. After 20 mins, the strip was detected by the reader.

8. Strip Test System Based on Single Photon Avalanche Detector

Figure 4:
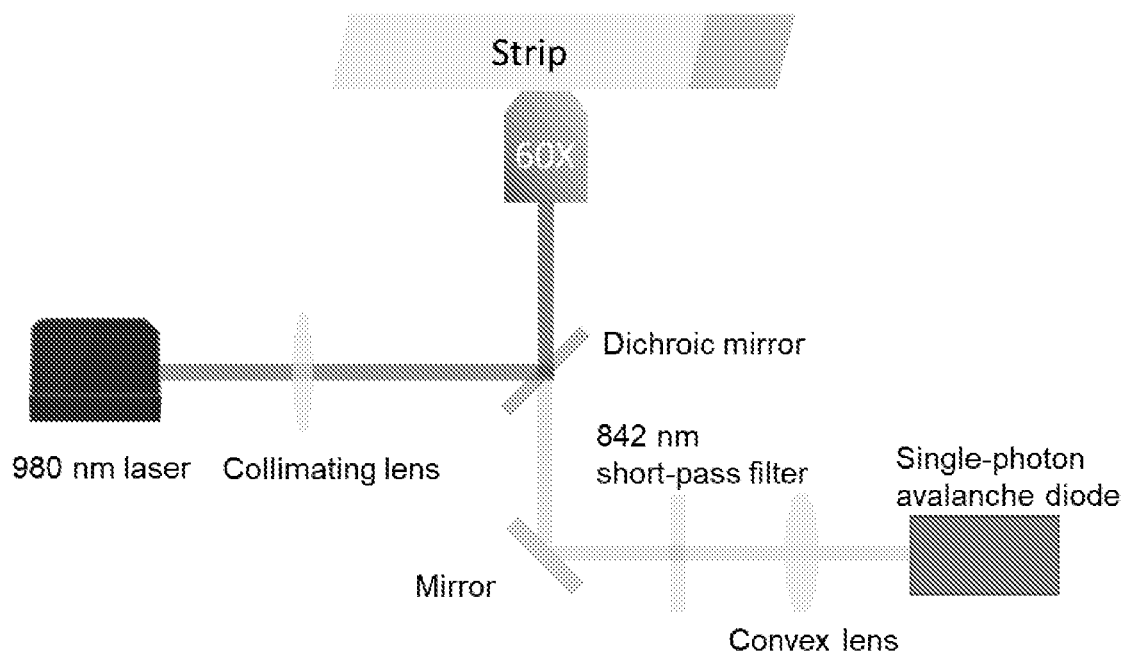
FIG. 4: Optical layout of strip test system based on single photon counting detector.

To read the emission signal from the UCNP reporters on the strips, a purpose-built scanning confocal system was constructed (FIG. 4). A 976 nm laser was used to excite the UCNPs, with a home built power control unit including a half wave plate and a polarizer. The emission of the UCNPs was collected by an objective lens (60x, NA 0.85 Edmund), and then focused by a tube lens to an optical fibre, which was linked to a single photon avalanche detector (SPA©), x-y movement of the stage was used to read 10 different points of one testing area.

9. Calculation of LOD

3σ methods were used to calculate the LOD of the strip test system. Noise N=background+3 SD(background) and liner fit S/N was set with target concentrations. The LOD is the concentration when S/N=1.

Example 1

To obtain smaller and brighter UCNPs, two types of inert shell passivated UCNPs highly doped with Er$^{3+}$ and Tm$^{3+}$ (i.e. 8% Er/60% Yb@NaYF$_4$ and 8% Tm/60% Yb@NaYF$_4$) were synthesised, and their performance was evaluated against other UCNPs of the same size (i.e. 2% Er/20% Yb and 0.5% Tm/20% Yb). Ligand exchange was used to modify the surfaces of the UCNPs with carboxyl groups, followed by an EDC/NHS technique for conjugating antibodies. The uniformity of each UCNP sample was confirmed by TEM characterization (FIGS. 1, 5B and 5C). The successful conjugation of antibodies was confirmed by UV absorption spectra having a characteristic peak appearance at 280 nm (FIG. 2), and by dynamic light scattering which revealed a slight increase in size (Table 1).

Figure 6:
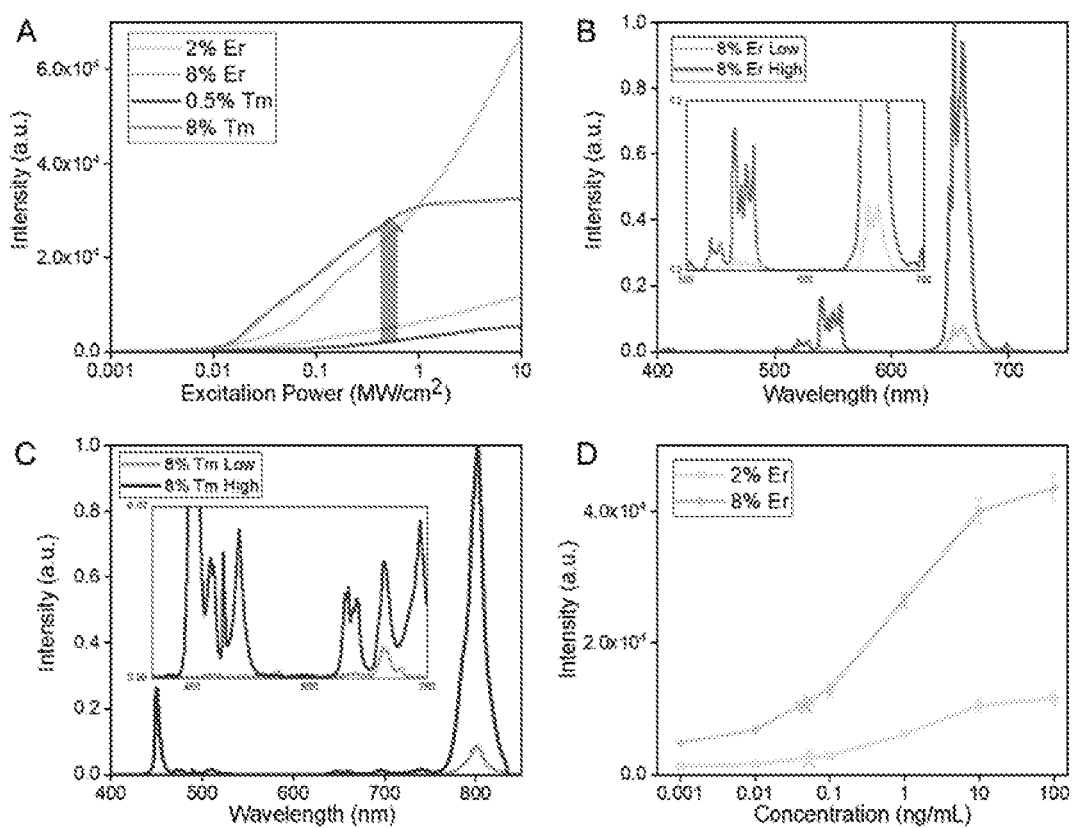
FIG. 6: A) Power dependent emission intensity profiles of single highly doped UCNP reporters and lower doped UCNPs. The red arrow indicates the power density at 0.5 MW/cm$^2$. B) Emission spectra of highly Er$^{3+}$ doped UCNP reporters under high (0.5 MW/cm$^2$) and low (0.01 MW/cm$^2$) excitation powers, C) Emission spectra of highly Tm$^{3+}$ doped UCNP reporters under high (0.5 MW/cm$^2$) and low (0.01 MW/cm$^2$) excitation powers. D) Fluorescence signal intensities of test area on strips when detecting different concentrations of target PSA using highly Er$^{3+}$ doped UCNP reporters and lower doped UCNPs. The stars mark the LODs.

The power-dependent properties of the as-prepared UCNP reporters was tested in respect of their emission intensities and spectrum profiles using a single nanoparticle characterization system (Wang et al. (2018) *Light Sci & Amp Appl* 2018: 7, 18007). With increasing excitation power density, the brightness of the highly doped UCNPs increased more substantially than the lower doped UCNPs (FIG. 6A). The enhancement ratios of the emission brightness for highly Er$^{3+}$ and Tm$^{3+}$ doped UCNPs were 5 times and 12 times greater than that of lower doped UCNPs when the power exceeds 0.5 MW/cm$^2$. As shown in FIG. 6B, the emission spectrum of highly Er$^{3+}$ doped UCNP reporters emit substantially more red at around 650 nm under higher excitation power, resulting in a bright yellowish emission. This paint mixing effect also occurs in the highly Tm$^{3+}$ doped UCNP reporters, with appearance in purple from the phone camera (power dependent spectrum profiles of lower doped UCNP reporters are shown FIG. 3).

Example 2

Highly Er$^{3+}$ doped UCNP reporters were compared to lower doped UCNPs by detecting different concentrations of target PSA on lateral flow strips. At an excitation power density of 0.5 MW/cm$^2$, the signals from the test area and background area were recorded by a single photon counting detector. As shown in FIG. 6D, the signal from the highly doped UCNP reporters was much higher than the signal from the lower doped UNCPs, and the brightness enhancement ratio was consistent with the single nanoparticle characterization results. Despite the difference in brightness, both reporters show the same PSA limit of detection (LOD) of 50 pg/mL, Only the highly doped UCNP reporters provide sufficient brightness for a normal phone camera.

Example 3

Figure 7:
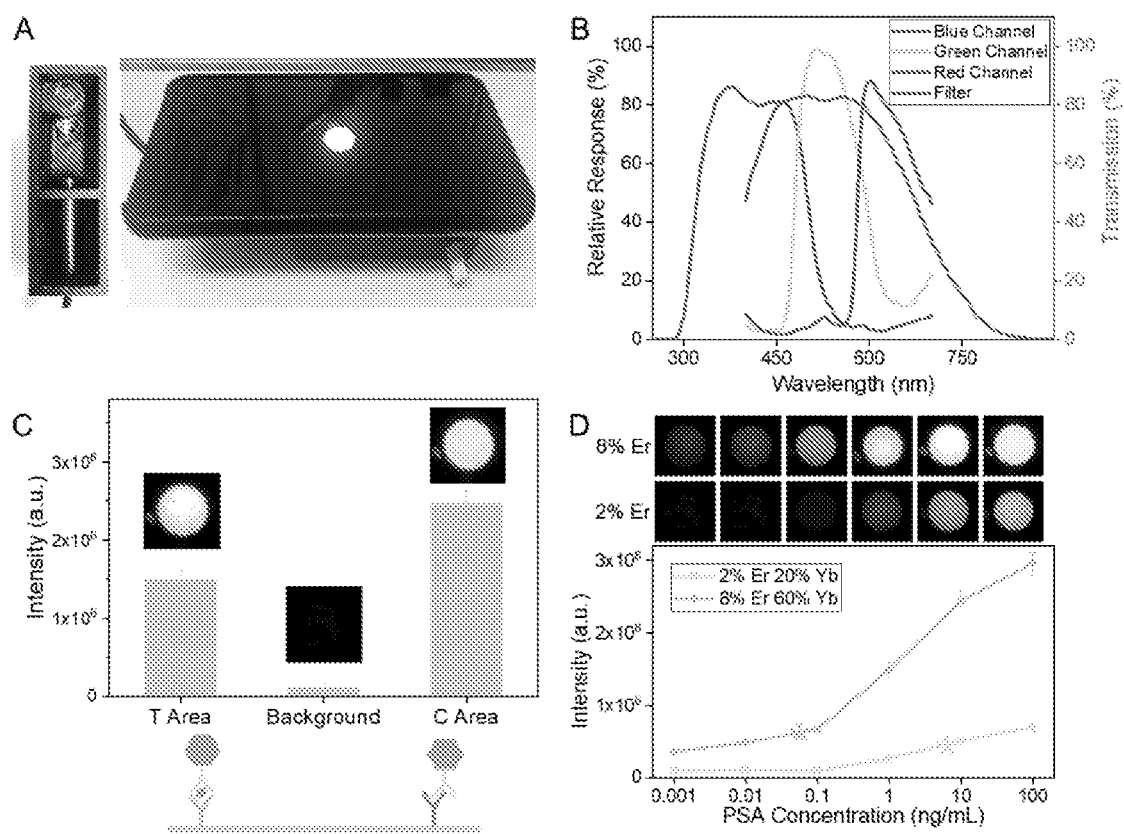
FIG. 7: A) Photos of a 3D-printed box for housing optics (left) and the working state of the phone-based LFS device (right). B) Spectral response (coloured lines) of the phone camera CMOS (Sony IMX-214) and the transmission curve (grey line) of KG-3 absorbing glass. C) Representative result from a typical PSA assay showing the signals from testing area, background and control area, D) Detection of different concentrations of target PSA on strips using highly Er$^{3+}$ doped UCNP reporters and lower doped UCNPs. The stars mark the LODs.

A compact device enclosed by a 3D-printed small housing was constructed as shown in FIG. 5A and FIG. 7A. The device used a 980 nm 300 mw laser diode as the light source, two hemisphere lenses—one to focus the excitation light beam to the strip and the other for collecting the emission signal to the phone camera—and a low-cost KG-3 heat absorbing glass as the short pass filter to remove laser scattering. The spectral response of the phone camera CMOS (Sony IMX-214) and the transmission curve of the KG-3 glass indicates that the phone camera can read most of the visible emission signals from the highly doped UCNP reporters with only a negligible amount of excitation scattering light being detected (FIG. 7B).

For demonstration purposes, the optics and camera setting were fixed, but the strip was moved from one side to another at a constant speed so that the average fluorescence intensity values of the testing area, the control area and the background area could be extracted from video analyses (FIG. 7C). Referring to FIG. 7D, the highly doped UCNP reporters provided detectable signals when the target concentration was low, whereas the lower doped UCNPs did not. The LOD for PSA using highly $Er^{3+}$ doped UCNP reporters was 61 pg/mL, whereas the LOD using the lower doped UCNPs was 8.5 ng/mL.

Example 4

Figure 8:
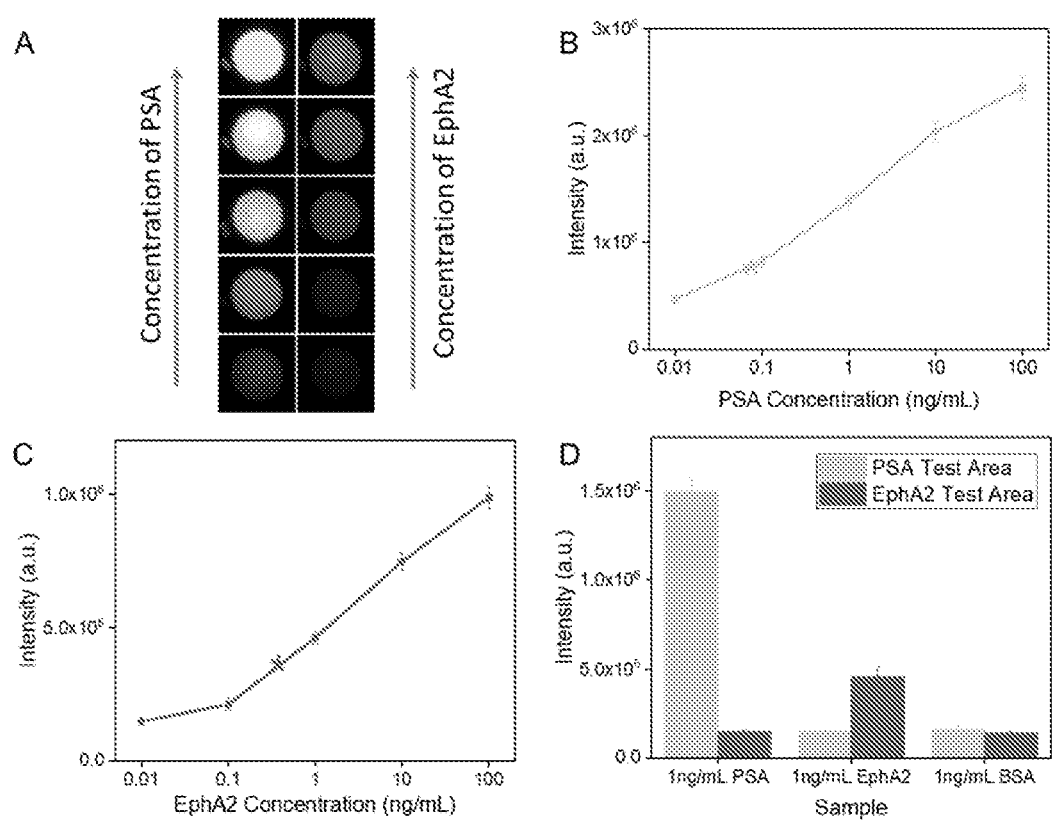
FIG. 8: A) Photos of two-colour LFS assay for testing different concentrations of PSA and EphA2. B) Fluorescence intensities of PSA test area for detecting different concentrations of PSA. C) Fluorescence intensities of EphA2 test area for detecting different concentrations of EphA2. D) Specificity evaluation of two-colour LFS for 1 ng/mL PSA, EphA2 and BSA. The stars mark the LODs.

Highly $Er^{3-}$ and $Tm^{3+}$ doped UCNP reporters were then used in a single strip for simultaneous testing of PSA and EphA2 target analytes. To this end, highly $Er^{3+}$ doped UCNPs were modified with anti-PSA antibodies, and highly $Tm^{3+}$ doped UCNPs were modified with anti-EphA2 antibodies. FIG. 8A shows the results from testing two targets. The yellowish and purple colours indicate the presence of PSA and EphA2 respectively, and the brightness increases with increasing target concentration. The two-colour LFS system achieved a LOD of 89 pg/mL for PSA (FIG. 88), demonstrating that the system maintains the high sensitivity that was achieved from the single-color system. The LOD for EphA2 was 400 pg/mL (FIG. 8C). As the emission energy of highly $Tm^{3+}$ doped UCNP reporters is around 800 nm (FIG. 6C), which is beyond the range of detection optics and phone camera (FIG. 7B), the signal intensity is lower. The specificity of a two-colour LFS system was further evaluated by testing two targets, PSA and EphA2 separately, with BSA as an interfering analyte. Compared to the control groups, all of the positive groups showed much higher intensity. The results indicate that there are negligible cross-interactions.

Although the invention has been described with reference to specific embodiments, it will be appreciated by those skilled in the art that the invention may be embodied in many other forms.

The invention claimed is:

1. A method for determining the quantity of at least one analyte in a sample, the method comprising:
   providing a lateral flow strip comprising a capture moiety and a conjugate comprising a detection moiety capable of binding the at least one analyte and highly-doped upconversion nanoparticles for visualising interaction of the at least one analyte and the capture moiety;
   applying the sample to the lateral flow strip such that the conjugate binds the analyte to provide a bound analyte that is subsequently captured by the capture moiety;
   providing a testing device comprising an excitation light source configured to elicit a detectable signal from the highly-doped upconversion nanoparticles and a detector to capture the detectable signal, the testing device being capable of receiving the lateral flow strip;
   inserting the lateral flow strip to which the sample has been applied into the testing device;
   irradiating an area of the lateral flow strip comprising the highly-doped upconversion nanoparticles with a beam of light so as to elicit a detectable signal from the highly-doped upconversion nanoparticles; and detecting the detectable signal and determining the quantity of the at least one analyte in the sample based on the detectable signal, wherein the highly-doped upconversion nanoparticles comprise a host material, a sensitiser which is $Yb^{3+}$ or $Er^{3+}$, and an activator which is $Er^{3+}$, $Tm^{3+}$, or $Ho^{3+}$, and wherein the sensitiser is present in a concentration of at least 30 mol % and the activator is present in a concentration of at least 3 mol %, or
   wherein the highly-doped upconversion nanoparticles comprise a host material and an activator which is $Er^{3+}$ in a concentration of at least 50-8 mol %.

2. The method of claim 1, wherein the sensitiser is present in a concentration of 30 mol % to 80 mol %.

3. The method of claim 1, wherein the sensitiser is $Yb^{3+}$.

4. The method of claim 1, wherein the host material is an alkali fluoride, an oxide or an oxysulfide.

5. The method of claim 4, wherein the host material is selected from the group consisting of: $NaGdF_4$, $Ca_2F$, $NaYF_4$, $LiYF_4$, $NaLuF_4$, $LiLuF_4$, $KMnF_3$ and $Y_2O_3$, including combinations thereof.

6. The method of claim 1, wherein the highly-doped upconversion nanoparticles are inert shell passivated.

7. The method of claim 1, wherein the highly-doped upconversion nanoparticles are 8% Er/60% Yb@$NaYF_4$, 8% Tm/60% Yb@$NaYF_4$ or 40% Er/60% Yb@$NaYF_4$ or 100% Er@$NaYF_4$.

8. The method of claim 1, wherein the capture moiety and/or the detection moiety include one or more of: an antibody, an aptamer, an epitope, a nucleic acid or a molecular imprinted polymer.

9. The method of claim 1, wherein the testing device further comprises a lens or an array of lenses interposed between the excitation light source and the lateral flow strip so to focus the beam of light on the lateral flow strip, or wherein the testing device further comprises a lens or an array of lenses interposed between the lateral flow strip and the detector so as to focus the signal on the detector.

10. The method of claim 1, wherein the detector is a camera or a single element detector.

11. The method of claim 10, wherein the detector is a smart phone camera.

12. The method of claim 1, wherein the detectable signal is visible light or infrared light.

13. The method of claim 1, wherein the excitation light source is a laser diode or a near IR light source.

14. The method of claim 1, wherein the beam of light has a power density of at least about 0.001 $MW/cm^2$.

15. The method of claim 1, wherein the area irradiated is between about 1 $\mu m^2$ and about 10,000,000 $\mu m^2$.

16. The method of claim 1, wherein the sample is a biological sample.

17. The method of claim 1, wherein the analyte is a biomarker.

18. The method of claim 1, wherein the method comprises determining the quantity of a plurality of analytes.

19. The method of claim 1, wherein the quantity of the at least one analyte in the sample is determined by fitting intensity of an image captured by the detector with a pre-set intensity-concentration curve for the analyte.

* * * * *

UNITED STATES PATENT AND TRADEMARK OFFICE
CERTIFICATE OF CORRECTION

PATENT NO. : 12,228,570 B2
APPLICATION NO. : 17/279576
DATED : February 18, 2025
INVENTOR(S) : Dayong Jin et al.

Page 1 of 1

It is certified that error appears in the above-identified patent and that said Letters Patent is hereby corrected as shown below:

In the Claims

Claim 1, Column 13, Line 61, replace "elicita" with "elicit a"

Claim 1, Column 14, Line 16, replace "50-8 mol %" with "8 mol %"

Signed and Sealed this
Fifteenth Day of July, 2025

Coke Morgan Stewart
*Acting Director of the United States Patent and Trademark Office*